(12) United States Patent
Young et al.

(10) Patent No.: US 7,108,848 B2
(45) Date of Patent: Sep. 19, 2006

(54) FUNGICIDAL GEL AND METHOD FOR CONTROLLING NAIL FUNGI

(75) Inventors: John D. Young, Seminole, FL (US); Alberto Hoyo, Miami, FL (US)

(73) Assignee: Aqua Med, Inc., Seminole, FL (US)

( * ) Notice: Subject to any disclaimer, the term of this patent is extended or adjusted under 35 U.S.C. 154(b) by 99 days.

(21) Appl. No.: 10/894,769

(22) Filed: Jul. 20, 2004
(Under 37 CFR 1.47)

(65) Prior Publication Data

US 2006/0018850 A1     Jan. 26, 2006

(51) Int. Cl.
*A61K 8/00* (2006.01)
*A61K 8/18* (2006.01)
*A61K 9/00* (2006.01)
*A61Q 3/00* (2006.01)
*A01N 59/08* (2006.01)

(52) U.S. Cl. .................. 424/61; 424/677; 424/400; 424/484

(58) Field of Classification Search .............. None
See application file for complete search history.

(56) References Cited

U.S. PATENT DOCUMENTS

| 3,893,943 | A | 7/1975 | Willard, Sr. |
| 4,029,770 | A | 6/1977 | Willard, Sr. |
| 6,416,790 | B1 * | 7/2002 | Young .................. 424/681 |
| 6,692,775 | B1 * | 2/2004 | Young .................. 424/681 |
| 2001/0043954 | A1 | 11/2001 | Sweet |
| 2003/0064959 | A1 * | 4/2003 | Sawada et al. ........... 514/54 |
| 2004/0156874 | A1 * | 8/2004 | Glassman et al. ........ 424/401 |

* cited by examiner

*Primary Examiner*—Carlos A. Azpuru
*Assistant Examiner*—David Vanik
(74) *Attorney, Agent, or Firm*—Larson & Larson, PA; Herbert W. Larson

(57) ABSTRACT

A gel formulation is combined with a fungicidal concentrate which is a liquid mixture of about 1.2 to 16 ml parts by volume of ultra pure water having an electrical resistance of 16–26 megohms, total dissolved solids of less than 0.04 parts per million and a specific conductance of less than 0.10 mho with about 1.2 to 16 parts by volume of Willard Water as prepared in accordance with U.S. Pat. No. 3,893,943, together with one liter of a gel formulation ingredient containing 10% by weight urea, based on the weight of the gel formulation. The fungicidal liquid concentrate is applied directly to a fungal nail to soften the fungal nail and control the growth of fungi.

9 Claims, No Drawings

FUNGICIDAL GEL AND METHOD FOR CONTROLLING NAIL FUNGI

FIELD OF THE INVENTION

This invention relates to a catalyst called Willard Water. More particularly, it refers to a fungicidal gel formed from a concentrate of the catalyst and ultra pure water mixed with urea in a gel composition or formulation together with the use of the resulting fungicidal gel concentrate to control fungi under growing nails.

BACKGROUND OF THE INVENTION

Willard Water is set forth in U.S. Pat. No. 3,893,943 as a novel catalyst and its preparation is therein described. Willard Water has a poor shelf life insofar as its use in a fungicidal solution. A concentrate is needed that will provide an extended shelf life and will be useful to treat a nail bed that is contaminated with fungi.

SUMMARY OF THE INVENTION

The present invention solves the above problems by providing a fungicidal gel concentrate. The concentrate is made with a liquid mixture ratio of about 1.2 to 16 ml of Willard Water to about 1.2 to 16 ml of ultra pure water having an electrical resistance of 16–26 megohms, total dissolved solids of less than 0.04 parts per million and a specific conductance of less than 0.10 mho. The Willard Water employed in the concentrate is described in U.S. Pat. No. 3,893,943. The concentrate as a gel formulation additionally contains about one liter methylcellulose, depending on the thickness of the gel (ointment) desired. Any type of gel can be used as long as it is not oil based. About 5 to 40% by weight urea based on the weight of the methylcellulose completes the concentrate. This is used to apply to the nail bed of patients to control fungal contaminations. A gel for treatment of nail beds is formed from the gel concentrate at a pH of 7.5 to 10. The concentrate of this invention has a shelf life in a plastic container of at least two and one half years compared to a shelf life of Willard Water combined with distilled water of less than seven months.

DETAILED DESCRIPTION OF THE INVENTION

The fungicidal concentrate of this invention is made from 1.2 to 16 parts by volume of Willard Water made according to the description of the catalyst described in U.S. Pat. No. 3,893,943, incorporated herein by reference, to 1.2 to 16 parts by volume of ultra pure water.

The ultra pure water is made by first passing potable water through a 5 micron sediment filter and then through a granulated activated charcoal bed having a depth of about 20 cm. The water is then passed through a 1.2 cubic foot mixed bed deionizer resin such as SIBRON Model No. NM-60. The resulting treated water is passed twice through a standard reverse osmosis process utilizing Model FC-018A filters obtained from Water Link Technologies, Inc. and then through a 0.2 micron filter to obtain ultra pure water having an electrical resistance of 16–26 megohms, total dissolved solids of less than 0.04 parts per million and a specific conductance of less than 0.10 mho.

The ultra pure water is mixed in a holding drum with the Willard Water at varying ratios of 1.2–16 parts by volume depending upon the fungi for which control is sought.

This mixture is incorporated with one liter of methylcellulose composition containing about 2% methylcellulose and 5 to 40% by weight of urea based on the weight of the methylcellulose. This mixture is used for treatment of Tinea rubrum, Epidermophyton floreusum and Trichophyton gallinae fungi.

For treatment of nail bed fungi, the gel formulation will contain sodium silicate, sulfate of ester of oil of Euphorbiaceae, magnesium, calcium and chloride ions. The methylcellulose can be substituted with other gel formulation ingredients such as xanthan gum, methylparaben, potassium sorbate and sodium benzoate. The gel formulation should be buffered preferably at about a pH of 9.0 to 10.0.

The gel concentrate is applied twice a day for two weeks directly to a patient's affected nail to soften fungal nails and allow silicate from the product to act on the nail bed, thus stopping the growth of fungi. After two weeks, there was a change in fungal load; the nail got softer, not as thick and became clearer.

Having thus described the invention what is claimed and desired to be secured by Letters Patent is:

1. A fungicidal concentrate in a gel formulation comprising:

(a) a liquid mixture ratio of about 1.2 to 16 parts by volume ultra pure water having an electrical resistance of 16–26 megohms, total dissolved solids of less than 0.04 parts per million and a specific conductance of less than 0.10 mho;

(b) mixed with 1.2 to 16 parts by volume of catalyst micelles prepared by admixing a water soluble alkali metal silicate with an aqueous medium containing a dissolved substance which is a source of calcium ion and a dissolved substance which is a source of magnesium ion;

the aqueous medium containing the dissolved substances in amounts to provide between about $1 \times 10^{-4}$ and $1 \times 10^{-1}$ mole per liter each of calcium ion and magnesium ion;

the aqueous medium containing the dissolved substances in amounts to provide a molar ratio of calcium ion to magnesium ion between about 2.0:1.0 and 1.0:2.0;

reacting the alkali metal silicate with the dissolved substances providing calcium ion and magnesium ion to produce an aqueous suspension of finely divided particles of the reaction product;

admixing a micelle-forming surfactant with the aqueous medium in an amount to form catalyst micelles comprising the finely divided particles of the reaction product upon agitating the aqueous medium; and agitating the aqueous medium containing the finely divided particles of the reaction product and surfactant to form the catalyst micelles; and (c) mixing the product of (a) and (b) with one liter of a gel formulation ingredient and 5–40% by weight urea based on the weight of the gel formulation ingredient.

2. The fungicidal concentrate in a gel formulation according to claim 1 wherein the one liter gel formulation ingredient contains a 2% methylcellulose composition.

3. The fungicidal concentrate in a gel formulation according to claim 1, wherein the one liter gel formulation contains sodium silicate, sulfate of ester of oil of Euphorbiaceae, magnesium, calcium and chloride ions.

4. The fungicidal concentrate in a gel formulation according to claim 1 wherein the gel formulation ingredient is selected from the group consisting of methylcellulose, xanthan gum, methylparaben, potassium sorbate and sodium benzoate buffered to a pH of 7.5 to 10.

5. Method of treating fungal nails comprising applying a fungicidal concentrate in a gel formulation according to claim 1 to the fungal nails.

6. The method according to claim 5 wherein a cotton gauze is applied over the fungicidal concentrate in a gel formulation.

7. Method of treating fungal nails comprising applying a fungicidal concentrate in a gel formulation according to claim 2 to the fungal nails.

8. Method of treating fungal nails comprising applying a fungicidal concentrate in a gel formulation according to claim 3 to the fungal nails.

9. Method of treating fungal nails comprising applying a fungicidal concentrate in a gel formulation according to claim 4 to the fungal nails.

* * * * *